United States Patent [19]

Schohe-Loop et al.

[11] Patent Number: 5,468,882
[45] Date of Patent: Nov. 21, 1995

[54] 2-AMINOMETHYL-CHROMANS

[75] Inventors: Rudolf Schohe-Loop, Wuppertal; Hans-Georg Heine, Krefeld; Bodo Junge, Wuppertal; Thomas Glaser, Overath; Jean M. V. De Vry, Roesrath; Wolfgang Dompert; Henning Sommermeyer, both of Cologne, all of Germany

[73] Assignee: Bayer Aktiengesellschaft, Leverkusen, Germany

[21] Appl. No.: 215,995

[22] Filed: Mar. 22, 1994

Related U.S. Application Data

[62] Division of Ser. No. 963,203, Oct. 19, 1992, Pat. No. 5,318,988.

[30] Foreign Application Priority Data

Oct. 28, 1991 [DE] Germany ............................ 41 35 474.5

[51] Int. Cl.[6] .................................................. C07D 311/74
[52] U.S. Cl. .................................................. 549/407
[58] Field of Search ................................................ 549/407

[56] References Cited

U.S. PATENT DOCUMENTS

| 4,321,270 | 3/1982 | Sundeen | 549/407 |
|---|---|---|---|
| 5,126,367 | 6/1992 | Stack et al. | |
| 5,137,901 | 8/1992 | Junge et al. | 514/373 |

FOREIGN PATENT DOCUMENTS

| 0325964 | 1/1989 | European Pat. Off. | |
|---|---|---|---|
| 0334429 | 3/1989 | European Pat. Off. | |
| 0369874 | 5/1990 | European Pat. Off. | 549/407 |

OTHER PUBLICATIONS

Ram Pratap, *Indian Journal of Chemistry*, 11 May 1981, pub. Dec. 1981, pp. 1063–1067.
W. U. Dompert, Naunyn–Schmiedeberg's *Arch Pharmacol*, 1985, pp. 467–470.
Eckard Weber, *Proc. Natl. Acad. Sci. USA*, vol. 83, Nov. 1986, pp. 8784–8788.
Michael P. Kavanaugh, *Proc. Natl. Acad. Sci.*, Apr. 1988, pp. 2844–2848.
W. Clark Still, *J. Org. Chem.*, 1978, pp. 2923–2927.

*Primary Examiner*—Johann Richter
*Assistant Examiner*—John Peabody
*Attorney, Agent, or Firm*—William C. Gerstenzang; Sprung Horn Kramer & Woods

[57] ABSTRACT

Aminomethyl-chromans are obtained by alkylation of correspondingly substituted amines or by reductive amination of correspondingly substituted aldehydes. The aminomethyl-chromans can be used as active compounds in medicaments, in particular for the treatment of diseases of the central nervous system.

3 Claims, No Drawings

2-AMINOMETHYL-CHROMANS

This application is a divisional of application Ser. No. 07/963,203, filed Oct 19, 1992, now U.S. Pat. No. 5,318,988.

The invention relates to 2-aminomethyl-chromans, to processes for their preparation and to their use in medicaments, in particular as agents for combating diseases of the central nervous system.

Aminomethyltetralin and -chroman derivatives having a CNS activity are known from DE 39 01 814. Aminomethyldihydrobenzopyran derivatives which have a fungicidal action are furthermore described in DE 36 20 408. Benzofuran- and benzopyrancarboxamides are moreover known from EP 124 783.

The present invention now relates to new aminomethyl-chromans of the general formula (I)

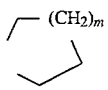

in which

A, B and D are identical or different and represent hydrogen, halogen, cyano, azido, nitro, difluoromethyl, trifluoromethyl, difluoromethoxy, trifluoromethoxy, hydroxyl or carboxyl, or represent straight-chain or branched alkyl, alkenyl, acyl or alkoxycarbonyl having in each case up to 8 carbon atoms, or represent a group of the formula $-NR^2R^3$, $-NR^4-L-R^5$ or $-OR^6$, wherein $R^2$, $R^3$ and $R^4$ are identical or different and denote hydrogen, straight-chain or branched alkyl having up to 8 carbon atoms, phenyl or benzyl, L denotes the —CO— or —SO$_2$— group, $R^5$ denotes straight-chain or branched alkyl having up to 8 carbon atoms or benzyl, or denotes aryl having 6 to 10 carbon atoms, which is optionally substituted by halogen, hydroxyl, nitro, cyano, trifluoromethyl or trifluoromethoxy or by straight-chain or branched alkyl or alkoxy having in each case up to 6 carbon atoms and $R^6$ denotes straight-chain or branched alkyl or alkenyl having in each case up to 8 carbon atoms, which are optionally substituted by cycloalkyl having 3 to 6 carbon atoms or phenyl, or A has one of the abovementioned meanings and B and D together form a 5- to 7-membered saturated, partly unsaturated or aromatic carbocyclic ring or heterocyclic ring having up to 2 hetero atoms from the series comprising S, N and O, where these can optionally have up to 2 carbonyl functions in the ring and which are optionally substituted by up to 2 identical or different substituents from the group comprising straight-chain or branched alkyl and alkoxy having in each case up to 6 carbon atoms, hydroxyl, cycloalkyl having 3 to 6 carbon atoms, phenyl, halogen, cyano and nitro, or in spiro form by a radical of the formula

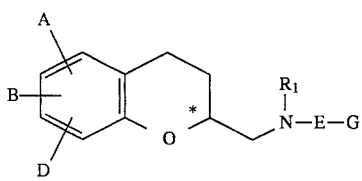

wherein m denotes the number 1 or 2,

E represents a direct bond, or represents straight-chain or branched alkylene, alkenylene or alkinylene having in each case up to 10 carbon atoms, which are optionally substituted by phenyl, G represents aryl having 6 to 10 carbon atoms, or represents a 5- to 7-membered, saturated or unsaturated heterocyclic ring which is not bonded via N and has up to 3 hetero atoms from the series comprising N, O and S, to which a further saturated, partly unsaturated or aromatic 6-membered carbocyclic ring can optionally also be fused, or represents cycloalkyl or a bridged bicarbocyclic ring having 3 to 15 carbon atoms, where all the cyclic rings are optionally substituted by up to 3 identical or different substituents, and in the case of the nitrogen-heterocyclic rings also via the nitrogen atom by one substituent, from the group comprising halogen, hydroxyl, nitro, cyano, difluoromethyl, trifluoromethyl, difluoromethoxy and trifluoromethoxy and straight-chain or branched alkyl and alkoxy having in each case up to 8 carbon atoms, the latter optionally being substituted by phenyl or phenoxy, or represents a radical of the formula

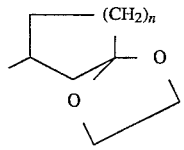

wherein n denotes the number 1 or 2, and $R^1$ represents hydrogen or represents straight-chain or branched alkyl having up to 8 carbon atoms, or represents the radical of the formula —E'—G', wherein E' and G' have the meaning given above for E and G and are identical to or different from these radicals, if appropriate in an isomeric form, and to salts thereof.

Physiologically acceptable salts are preferred in the context of tile present invention. Physiologically acceptable salts of the substituted 2-aminomethyl-chromans can be salts of the substances according to the invention with mineral acids, carboxylic acids or sulphonic acids. Salts which are particularly preferred are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are moreover salts of monovalent metals, such as alkali metals, and the ammonium salts. Salts of sodium, potassium and ammonium are preferred.

A heterocyclic ring is in general a 5- to 7-membered, preferably 5- to 6-membered, saturated or unsaturated ring, which can contain up to 2 oxygen, sulphur and/or nitrogen atoms as hetero atoms. 5- and 6-membered rings having one oxygen, sulphur and/or up to 2 nitrogen atoms are preferred. Preferred rings which may be mentioned are: thienyl, furyl, pyrrolyl, pyrazolyl, pyranyl, pyridyl, pyrimidyl, pyrazinyl, pyridazinyl, thiazolyl, oxazolyl, imidazolyl, isoxazolyl, pyrrolidinyl, piperidinyl, piperazinyl, tetrazolyl, morpholinyl or dioxanyl.

A bridged bicarbocyclic ring is in general 1-adamantyl, 2-adamantyl, norbornyl, bicyclo[2.2.3]octyl, bicyclo[4.2.0] octyl or tetracyclo[5.2.2.0.0]undecanyl. 1-Adamantyl, 2-adamantyl or norbornyl are preferred.

In the context of the present invention, the compounds according to the invention can be in various stereoisomeric forms. The compounds according to the invention exist in stereoisomeric forms which are either mirror images (enantiomers) or are not mirror images (diastereomers). The invention relates both to the antipodes and to the racemic forms as well as to the diastereomer mixtures. The racemic forms, like the diastereomers, can be separated into the stereoisomerically uniform constituents in a known manner [compare E. L. Eliel, Stereochemistry of Carbon Compounds, McGraw Hill, 1962].

Preferred compounds of the general formula (I) are those in which

A, B and D are identical or different and represent hydrogen, fluorine, chlorine, bromine, cyano, trifluoromethyl, difluoromethoxy, trifluoromethoxy or hydroxyl, or represent straight-chain or branched alkyl, alkenyl, acyl or alkoxycarbonyl having in each case up to 6 carbon atoms, or represent a group of the formula
—$NR^2R^3$, —$NR^4$—L—$R^5$ or —$OR^6$, wherein $R^2$, $R^3$ and $R^4$ are identical or different and denote hydrogen or straight-chain or branched alkyl having up to 6 carbon atoms, L denotes the —CO— or —$SO_2$— group, $R^5$ denotes straight-chain or branched alkyl having up to 6 carbon atoms or benzyl, or denotes phenyl, which is optionally substituted by fluorine, chlorine, bromine, trifluoromethyl, trifluoromethoxy or hydroxyl or by straight-chain or branched alkyl or alkoxy having in each case up to 4 carbon atoms, and $R^6$ denotes straight-chain or branched alkyl or alkenyl having up to 6 carbon atoms, which are optionally substituted by cyclopropyl, cyclopentyl, cyclohexyl or phenyl, or A has one of the abovementioned meanings and B and D together form a radical of the formula

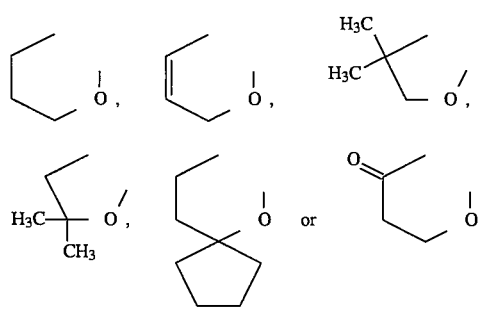

E represents a direct bond, or represents straight-chain or branched alkylene, alkenylene or alkinylene having in each case up to 8 carbon atoms, which are optionally substituted by phenyl, G represents phenyl, naphthyl, pyridyl, quinolyl, cyclopropyl, cyclobutyl, cyclopentyl, cyclohexyl, cycloheptyl, cyclooctyl or adamantyl, which are optionally substituted by up to 2 identical or different substituents from the group comprising hydroxyl, fluorine, chlorine, bromine, nitro, cyano, difluoromethyl, trifluoromethyl, difluoromethoxy and trifluoromethoxy and straight-chain or branched alkyl and alkoxy having in each case up to 6 carbon atoms, the latter optionally being substituted by phenyl or phenoxy, or represents a radical of the formula

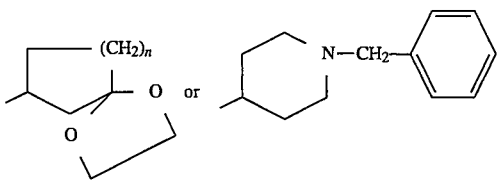

wherein n denotes the number 1 or 2, and $R^1$ represents hydrogen or represents straight-chain or branched alkyl having up to 6 carbon atoms, or represents the radical of the formula —E'—G', wherein E' and G' have the meaning given above for E and G and are identical to or different from these radicals, if appropriate in an isomeric form, and salts thereof.

Particularly preferred compounds of the general formula (I) are those in which

A, B and D are identical or different and represent hydrogen, fluorine, chlorine, bromine, cyano, trifluoromethyl, trifluoromethoxy or hydroxyl, or represent straight-chain or branched alkyl or alkenyl having in each case up to 4 carbon atoms, or represent a group of the formula —$NR^2R^3$ or —$OR^6$, wherein $R^2$ and $R^3$ are identical or different and denote hydrogen or straight-chain or branched alkyl having up to 4 carbon atoms and $R^6$ denotes straight-chain or branched alkyl or alkenyl having up to 4 carbon atoms, which are optionally substituted by cyclopropyl or phenyl, or A has one of the abovementioned meanings and B and D together form a radical of the formula

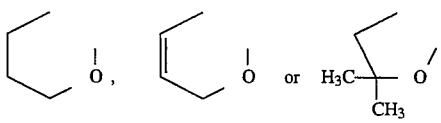

E represents a direct bond, or represents straight-chain or branched alkylene or alkenylene having in each case up to 7 carbon atoms, which are optionally substituted by phenyl, G represents phenyl, naphthyl, adamantyl, cyclopropyl, cyclopentyl, cyclohexyl, cycloheptyl or cyclooctyl, which are optionally substituted by fluorine, chlorine, bromine, hydroxyl, difluoromethyl, trifluoromethyl, difluoromethoxy or trifluoromethoxy or by straight-chain or branched alkyl or alkoxy having in each case up to 4 carbon atoms, the latter optionally being substituted by phenyl or phenoxy, or represents a radical of the formula

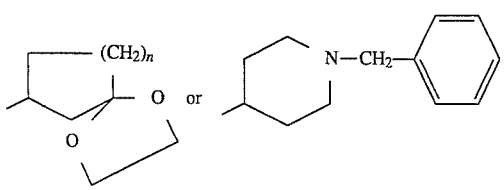

wherein n denotes the number 1 or 2, and $R^1$ represents hydrogen or represents straight-chain or branched alkyl having up to 4 carbon atoms, or represents the radical of the formula —E'—G', wherein E' and G' have the meaning given above for E and G and are identical to or different from these radicals, if appropriate in an isomeric form, and salts thereof.

Processes have furthermore been found for the preparation of the compounds of the general formula (I) according to the invention, which are characterised in that

[A1] compounds of the general formula (II)

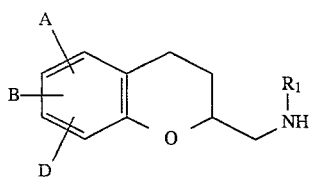
(II)

in which

A, B, D and $R^1$ have the abovementioned meaning, are alkylated with compounds of the general formula (III)

M—E—G  (III)

in which

M represents a typical leaving group, such as chlorine, bromine, iodine, tosylate or mesylate, or represents the group —OSO$_2$CF$_3$ and E and G have the abovementioned meaning, in inert solvents, if appropriate in the presence of a base and/or of a catalyst, or

[A2] compounds of the general formula (IV)

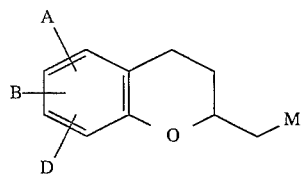
(IV)

in which

A, B, D and M have the abovementioned meaning, are alkylated with amines of the general formula (V)

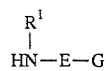
(V)

in which $R^1$, E and G have the abovementioned meaning, in inert solvents, if appropriate in the presence of a base and/or of a catalyst, or

[B1] aldehydes of the general formula (VI)

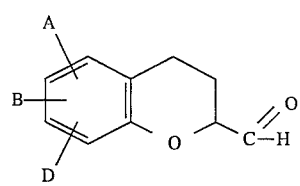
(VI)

in which

A, B and D have the abovementioned meaning, are alkylated reductively with amines of the general formula (V) in inert solvents, if appropriate in the presence of auxiliaries, or

[B2] in the case where E does not denote a direct bond, compounds of the general formula (II) are alkylated reductively either with aldehydes of the general formula (VII)

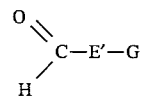
(VII)

in which

G has the abovementioned meaning and

E' has the abovementioned meaning of E but is shorter by one —CH$_2$— group, or, in the case where E represents a direct bond, with compounds off the general formula (VIIa)

in which

G' has the abovementioned meaning of G, but does not represent aryl, in inert solvents, if appropriate in the presence of auxiliaries, or

[C] compounds of the general formulae (VIII) or (IX)

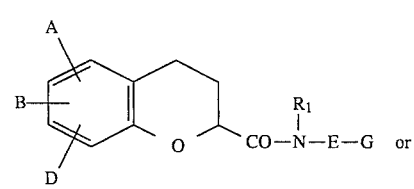
(VIII)

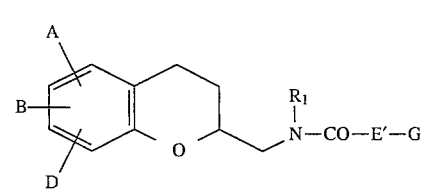
(IX)

in which

A, B, D, E, E', G and $R^1$ have the abovementioned meaning, are reduced by the customary method in inert solvents, if appropriate in the presence of auxiliaries, or

[D] in the case where E represents 3 to 6 methylene groups, compounds of the general formula (IIa)

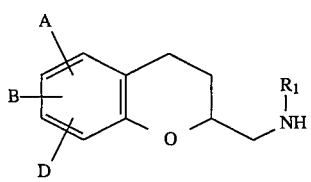

(IIa)

in which

A, B and D Stave the abovementioned meaning and $R^7$ has the abovementioned meaning of $R^1$, but does not represent hydrogen, are first reacted with either formaldehyde or formaldehyde derivatives and with compounds of the general formula. (X)

E"—G    (X)

in which

G has the abovementioned meaning and

E" represents a radical of the formula $HC\equiv C-(CH_2)_z$, wherein z denotes the number 0, 1, 2 or 3, in a reaction analogous to a Mannich reaction, and if appropriate hydrogenation by the customary method follows in a subsequent step, and in the case where $R^1$ does not represent hydrogen, the product is either alkylated by the customary method or alkylated reductively with formaldehyde ($R^1=CH_3$), as described above, and in the case where $R^1$ denotes hydrogen, the amine function is first blocked with suitable amino-protective groups during individual process steps, if appropriate, and these are removed by the customary method, preferably by hydrogenolysis, and if appropriate the substituents A, B, D and G are modified by the customary method.

The processes according to the invention can be illustrated by way of example by the following equation:

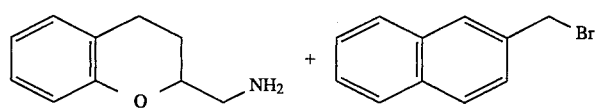

[A1]

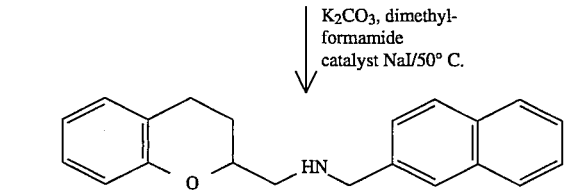

[A2]

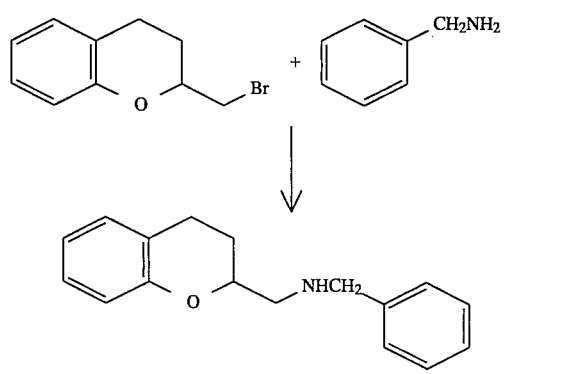

[B1]

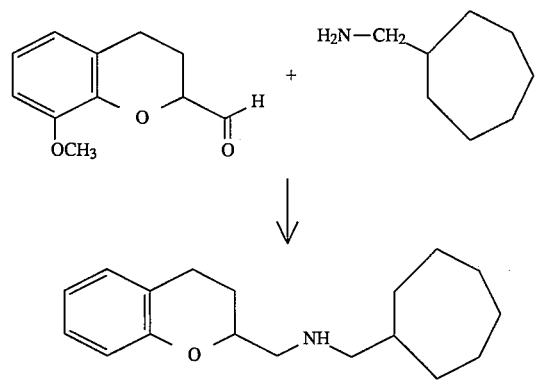

-continued

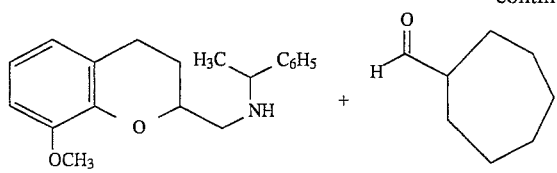

[B2]

↓ NaBH₃CN
HOAc
MeOH

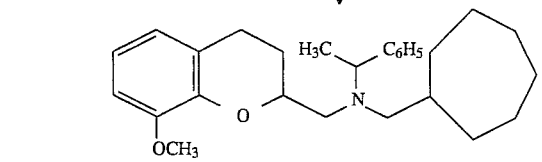

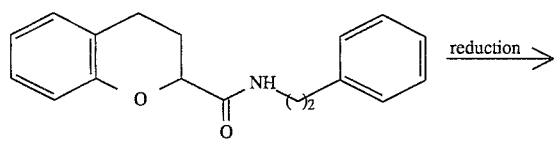  reduction →

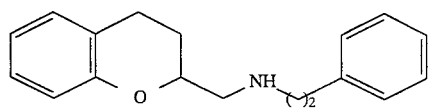

[C]

[D]

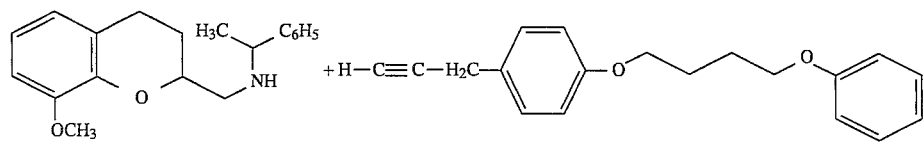

↓ 1.) formaldehyde
2.) hydrogenation

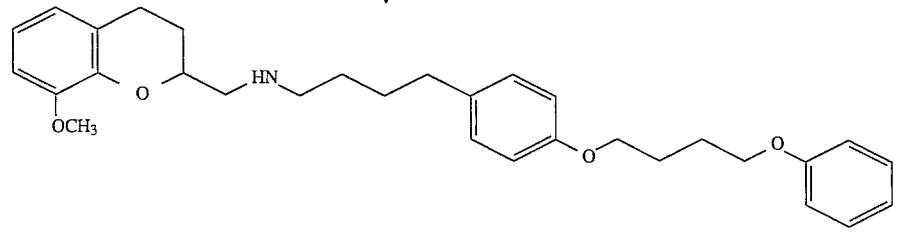

The customary solvents which do not change under the reaction conditions are suitable for the alkylation. These include, preferably, alcohols, such as methanol, ethanol, propanol or isopropanol, or ethers, such as diethyl ether, dioxane, tetrahydrofuran, glycol dimethyl ether or butyl methyl ether, or ketones, such as acetone or butanone, or amides, such as dimethylformamide or hexamethylphosphoric acid triamide, or dimethyl sulphoxide, acetonitrile, ethyl acetate or halogenohydrocarbons, such as methylene chloride, chloroform or carbon tetrachloride, or pyridine, picoline or N-methylpiperidine. Mixtures of the solvents mentioned can likewise be used. Methanol, ethanol, isopropanol, dimethylformamide and acetonitrile are preferred.

Suitable bases are the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholates, such as, for example, sodium methanolate or potassium methanolate or sodium ethanolate or potassium ethanolate, or organic amines, such as triethylamine, picoline or N-methylpiperidine, or amides, such as sodium amide or lithium diisopropylamide, or organometallic compounds, such as butyllithium or phenyllithium. Sodium carbonate and potassium carbonate, pyridine and triethylamine are preferred.

The alkylation is in general carried out in a temperature range from 0° C. to +150° C. preferably in a range from room temperature to +80° C.

The alkylation is in general carried out under normal pressure. However, it is also possible to carry out the reaction under increased or reduced pressure.

Alkali metal iodides are in general employed as reaction accelerators, and sodium iodide or potassium iodide is preferred.

The base is employed in this reaction in an amount of 1 to 5, preferably 1 to 2 mol, per mole of the compounds of the general formulae (II), (IIa) and (IV).

The reductive amination of the amines of the general formulae (II), (IIa) and (V) with the aldehydes of the general formulae (VI) and (VII) and the reductive alkylation of the compounds of the general formulae (II) and (IIa) with the ketones of the general formula (VIIa) are in general carried out in one step. In the case of a primary amine, the reaction can also be carried out in two stages, a Schiff's base or an enamine first being obtained.

The preparation of the Schiff's bases or enamines in the first step is carried out in inert organic solvents, if appropriate in the presence of a catalyst and if appropriate in the presence of a water-binding agent. The process according to the invention can be carried out in two steps, that is to say with isolation of the intermediate products. It is also possible to carry out the reduction as a one-pot process.

Suitable inert solvents here are the customary organic solvents which do not change under the reaction conditions. These include, preferably, alcohols, such as methanol, ethanol, propanol or isopropanol, or ethers, such as diethyl ether, butyl methyl ether, dioxane, tetrahydrofuran, glycol dimethyl ether or diethylene glycol diethyl ether, or halogenohydrocarbons, such as, for example, methylene chloride, chloroform or carbon tetrachloride, or hydrocarbons, such as benzene, toluene, xylene or petroleum fractions, or amides, such as dimethylformamide or hexamethylphosphoric acid triamide, or acetic acid. It is furthermore possible to use mixtures of the solvents mentioned. Methanol, ethanol, diethyl ether, tetrahydrofuran, toluene and chloroform are preferred.

Protonic acids are in general used as catalysts. These include, preferably, inorganic acids, such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

If appropriate, the water formed in the reaction can be removed as a mixture with the solvent used during or after the reaction, for example by distillation or by addition of water-binding agents, such as, for example, phosphorus pentoxide, or preferably by molecular sieves.

The reaction is in general carried out in a temperature range from 0° C. to 150° C., preferably from +20° C. to +100° C.

The reaction can be carried out under normal or increased pressure or under reduced pressure (for example 0.5 to 5 bar). It is in general carried out under normal pressure.

The reduction of the Schiff's bases or enamines in the second step is carried out either by hydrogen in water or in inert organic solvents, such as alcohols, ethers or halogenohydrocarbons, or mixtures thereof, with catalysts such as Raney nickel, palladium, palladium on animal charcoal or platinum, or with hydrides in inert solvents, if appropriate in the presence of a catalyst.

The reaction is preferably carried out with hydrides, such as complex borohydrides or aluminium hydrides. Sodium borohydride, lithium aluminium hydride or sodium cyanoborohydride are particularly preferably employed here.

Suitable solvents in this reaction are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the solvents mentioned.

Protonic acids are in general used as catalysts for the reduction with sodium cyanoborohydride. These include, preferably, inorganic acids, such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid.

In carrying out the processes according to the invention, it has proved favourable to carry out the reaction of the aldehydes (VI) and (VII) and ketones (VIIa) with the amines (II), (IIa) and (V) as a one-pot process in an inert solvent, preferably in acetic acid or alcohols, such as, for example, methanol, ethanol, propanol or isopropanol or mixtures thereof, in the presence of inorganic or organic acids, such as, for example, hydrochloric acid or acetic acid, and in the presence of a reducing agent, preferably of complex hydrides, such as, for example, sodium borohydride or sodium cyanoborohydride, if appropriate in the presence of a dehydrating agent, preferably a molecular sieve.

In the case where formaldehyde is used, the reaction is preferably carried out in water-miscible solvents, such as dioxane or tetrahydrofuran, using phosphorous acid or salts thereof as the reducing agent. Aqueous formaldehyde solution or trioxane can also be used as the source of formaldehyde. The reducing agent is employed in an equimolar amount to the aldehyde.

The reduction of the acid amides is carried out either by hydrogen in water or inert organic solvents, such as alcohols, ethers or halogenohydrocarbons or mixtures thereof, with, catalysts such as Raney nickel, palladium, palladium on animal charcoal or platinum, or with hydrides in inert solvents, if appropriate in the presence of a catalyst, or with boranes, diborane or their complex compounds.

The reactions are preferably carried out with hydrides, such as complex borohydrides, aluminum hydrides or sodium aluminium diethyl hydride. Sodium bis-(2-methoxyethoxy)dihydroaluminate, lithium aluminium hydride or diborane are particularly preferably employed here.

The reaction can be carried out under normal or increased pressure or under reduced pressure (for example 0.5 to 150 bar). The reactions with hydrides and boranes are in general carried out under normal pressure and the reactions with hydrogen are in general carried out under increased pressure.

The reduction is in general carried out in a temperature range from −50° C. up to the particular boiling point of the solvent, preferably from −20° C. to +90°C.

The reaction with formaldehyde and acetylene derivatives in a Mannich-like reaction is in general carried out in one of the abovementioned organic solvents which do not change under the particular reaction conditions, such as, for example, alcohols, ethers, hydrocarbons, halogenohydrocarbons and dimethylformamide and mixtures thereof. Tetrahydrofuran ant 1,4-dioxane are preferred.

Copper salts are in general employed as catalysts. Copper(II) acetate is preferred. Paraformaldehyde, trioxane, formalin solution and gaseous formaldehyde are employed as the source of formaldehyde. Paraformaldehyde is preferred.

The reaction is in general carried out in a temperature range from 0° C. up to the particular boiling point of the solvent, preferably from +20° C. to +70° C.

The reaction can be carried out under normal or increased pressure or under reduced pressure (for example 0.5 to 5 bar). It is in general carried out under normal pressure.

The amino-protective groups are in general removed with hydrogen in water or one of the abovementioned solvents, preferably water, methanol, ethanol, diethyl ether or tetrahydrofuran, in the presence of mineral acids, such as, for example, hydrochloric acid. Suitable catalysts are the abovementioned catalysts, preferably palladium and palladium on animal charcoal [compare Chem. and Biochemistry of the Amino Acids, G. C. Barrett, Chapman and Hall (1985)].

The catalyst is employed in an amount of 0.01 mol to 0.2 mol, preferably 0.05 mol to 0.15 mol, in each case based on the blocked compounds of the general formula (II).

The reaction can be carried out under normal or increased pressure or under reduced pressure (for example 0.5 to 25 bar). The reaction is in general carried out under normal pressure.

The reduction is in general carried out in a temperature range from −50° C. up to the particular boiling point of the solvent, preferably from −20° C. to +90° C.

The protective groups are removed from the corresponding ethers by the customary method, for example by treatment with protonic acids, such as hydrogen bromide, or by hydrogenolytic cleavage of the benzyl ethers in the abovementioned inert solvents in the presence of a catalyst using hydrogen gas [compare also Th. Greene: "Protective Groups in Organic Synthesis", J. Wiley/Sons, 1981, New York].

The compounds of the general formulae (III), (V), (VII) and (VIIa) are known per se or can be prepared by the customary method [compare Houben-Weyl "Methoden der organisthen Chemie (Methods of Organic Chemistry)" Volume XI/1 and XI/2, Beilstein 1, 594, 629, 662; Bellstein 2, 197, 201, 250, 278; and 3, 9, 10, 21, 461, 462, 463].

The compounds of the general formula (II) and (IIa) are known per se [compare Indian J. Chem. Sect. B, 20B (12), 1063-7; DE 39 01 814], or can be prepared by the customary method from the corresponding ketones by reductive amination, alkylation or reductive alkylation.

The compounds of the general formulae (IV) and (VI) are known per se or can be prepared by the customary method [compare, for example, U.S. Pat. No. 4,957,928; EP 252 005; EP 334 429; EP 145 067].

The compounds of the general formula (VIII) are known in some cases [compare, for example: U.S. Pat. No. 4,238, 506; DE 2 604 560], while those of the general formula (IX) are new and are formed by reaction of the particular carboxylic acids, or activated stages thereof, with the compounds of the general formulae (II) or (V).

The compounds of the general formula (X) are new and can be prepared, in a concrete case, for example, by preparing 3-[4-(4-phenoxybutoxy)phenyl]propine from 4-bromophenol in 2 stages by reaction with 4-bromobutylphenyl ether in the presence of an alkali metal carbonate in acetone and then reacting the reaction product with methoxyallene under Cu(I) catalysis.

The compounds according to the invention can be used as active compounds in medicaments. The substances according to the invention have a particularly high affinity for cerebral 5-hydroxy-tryptamine receptors of the 5-HT$_1$ type.

They have agonistic, partly agonistic or antagonistic actions on the serotonin receptor. Compared with structurally related known compounds, the compounds according to the invention surprisingly have a high affinity for sigma receptors.

The compounds described in the present invention are thus active compounds for combating diseases which are characterised by disturbances in the serotoninergic system, in particular involving receptors which have a high affinity for 5-hydroxytryptamine (5-HT$_1$ type). They are therefore suitable for the treatment of diseases of the central nervous system, such as states of anxiety, stress and depression, and sexual dysfunctions and sleep disturbances of central nervous origin, and for regulating pathological disturbances in the consumption of food, luxury items and addictive agents. They are furthermore suitable for eliminating cognitive deficits, for improving learning and memory performance and for the treatment of Alzheimer's disease. They are also suitable for combating psychoses (for example schizophrenia and mania). Compared with known neuroleptics, they have a lower potential for side effects.

These active compounds are furthermore suitable for modulation of the cardiovascular system. They also intervene in regulation of cerebral blood circulation and are therefore effective agents for combating migraine. They are also suitable for the prophylaxis and control of the consequences of cerebral infarctions (apoplexia cerebri), such as apoplexy and cerebral ischaemias. In addition, the compounds according to the invention can be employed for the treatment of acute cranio-cerebral trauma and also for combating pain. Moreover, they are suitable for combating disturbances in the immune system.

1. Affinity for the 5-TH$_1$ receptor

The high affinity of the compounds according to the invention for 5-hydroxytryptamine receptors of the sub-type 1 is shown by way of example in Table A.

The values given are data which have been determined from receptor binding studies using calf hippocampus membrane preparations. $^3$H-Serotonin was used as the radioactively labelled ligand for this.

TABLE A

| Compound of Example | K$_i$ (nmol/l) |
|---|---|
| 23 | 5 |
| 13 | 36 |
| 18 | 3 |
| 22 | 6 |

2. Affinity for the 5HT$_{1A}$ receptor [W. U. Dompert et al., Naunyn-Schmeideberg's Arch. Pharmacol. (1985), 328, 647–470].

In this test, the binding of $^3$H-ipsapiron to 5-HT$_{1A}$ receptors in calf hippocampus membranes is measured. It was found that the compounds according to the invention compete with the radioligand for binding and inhibit this.

TABLE B

| Compound of Example | K$_i$ (nmol/l) |
|---|---|
| 17 | 0.7 |
| 28 | 2.3 |
| 31 | 4.2 |
| 35 | 28 |
| 36 | 0.5 |

3. Affinity for the sigma receptor

The sigma receptor binding test is described in detail by E. Weber et al. (1986), Proc. Natl. Acad. Sci. 83, 8784–8788 and M. P. Kavanaugh et al., (1988), Proc. Natl. Acad. Sci. 85, 2844. In this test, the binding of 3-di-o-tolylguanidine (DTG) to calf hippocampus membranes is measured.

TABLE C

| Compound of Example | $K_i$ (nmol/l) |
|---|---|
| 1 | 7 |
| 23 | 30 |
| 13 | 5 |
| 17 | 8 |
| 31 | 16 |
| 36 | 25 |

In this binding test, $IC_{50}$ values which indicate the test substance concentration at which 50% of the binding of the radioligand is suppressed are determined. The inhibition constants $K_i$ are calculated from these taking into account the dissociation constants and the concentration of of radio-ligands.

The present invention also relates to pharmaceutical formulations which contain, in addition to inert, nontoxic, pharmaceutically suitable auxiliaries and excipients, one or more compounds of the general formula (I), or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight of the total mixture.

The pharmaceutical formulations can also contain other pharmaceutical active compounds in addition to the active compounds of the formula (I).

The abovementioned pharmaceutical formulations can be prepared in the customary manner by known methods, for example with the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, it may be advantageous, if appropriate, to deviate from the amounts mentioned, in particular as a function of the nature and body weight of the subject treated, of the behaviour of the individual towards the medicament, of the nature and severity of the disease, of the nature of the formulation and administration and of the time or interval at which administration takes place.

The particular $R_f$ values given were—unless noted otherwise—determined by thin layer chromatography on silica gel (aluminium foil, silica gel 60 F 254, E. Merck). The substance spots were visualised by viewing under UV light and/or by spraying with 1% strength potassium permanganate solution.

The flash chromatography was carried out on silica gel 60, 0.040–0.064 mm, E. Merck (see Still et al., J. Org. Chem. 43, 2923, 1978; for simpler separation problems, see Aldrichimica Acta 18, 25, 1985). Elution with solvent gradients means: starting with the pure, non-polar component of the solvent mixture, the polar component of the mobile phase is admixed in an increasing amount, until the desired product is eluted (monitoring by thin layer chromatography).

For all the products, the solvent was distilled off under a final pressure of about 0.1 mmHg. Salts were kept over potassium hydroxide and/or phosphorus pentoxide under this pressure overnight.

Solvent mixture
1=methylene chloride/$C_2H_5OH$/$NH_3$ (200:10:1)
2=toluene/2-propanol (3:1)
3=toluene/ethyl acetate (3:1)
4=toluene/ethyl acetate (1:1)
Starting compounds

EXAMPLE I

N-[1-(R)-Phenylethyl]-N-(S)-chroman-2-yl-methyl)-cycloheptanecarboxamide

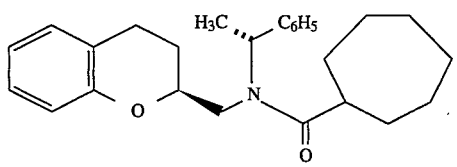

N-[1-(R)-Phenylethyl]-2-(S)-aminomethylchroman (3.0 g; 11 mmol) (prepared analogously to EP 352 613, Example 92) is dissolved in 33 ml of pyridine, and 2.8 g (17 mmol) of cycloheptanecarbonyl chloride are added. After 3 hours at 50° C., the mixture is concentrated and the residue is partitioned between water and toluene. Filtration over silica gel and concentration of the filtrate gives the amide as the crude product, which is reacted further. $R_f$=0.47 (toluene/ethyl acetate 3:1)

The compounds shown in Table I are obtained analogously to the instructions of Example I:

TABLE I

| Ex. No. | A | Y | G | $R_f$* |
|---|---|---|---|---|
| II | H | H₃C, C₆H₅ on CH with CH₂–N | cycloheptyl | 0.47³ |
| III | –OCH₃ | H₃C, C₆H₅ on CH with CH₂–N | cycloheptyl | 0.5³ |
| IV | –OCH₃ | H₃C, C₆H₅ on CH with CH₂–N | cycloheptyl | 0.50³ |

Example V

N-(1-Naphthylmethyl)-chroman-2-carboxamide

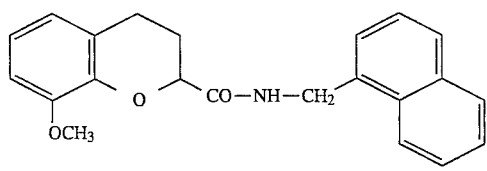

33.0 g (0.14 mol) of ethyl 8-methoxy-chroman-2-carboxylate (content 87%) are heated together with 25.8 g (0.16 mol) of 1-aminomethylnaphthalene and 0.05 g of potassium cyanide at 120° C. for 8 hours and then at 130° C. for 2 hours. After cooling, the mixture is diluted with 100 ml of toluene and this solution is introduced onto silica gel $K_{60}$. Elution with cyclohexane/ethyl acetate mixtures (100:0 to 75:25) gives the amide in the form of a viscous syrup (32.9 g, 68%), which can be further reacted directly.

The compounds shown in Table II are prepared analogously to the instructions of Example V:

Example XII

N-(Chroman-2-yl)methyl-cycloheptanecarboxamide

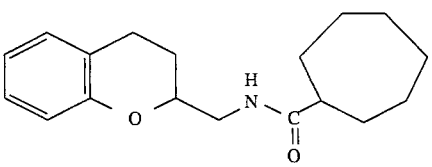

5.0 g (25 mmol) of 2-aminomethylchroman hydrochloride are dissolved in 50 ml of pyridine; 5.6 g (35 mmol) of cycloheptanecarbonyl chloride are added dropwise to this solution. After 1 hour at 50° C., the mixture is concentrated and the residue is partitioned between water and toluene/ethyl acetate 1:1. The organic phase is filtered over silica gel. The desired product is eluted with toluene/ethyl acetate 5:1. The amide obtained after concentration is further reacted directly.

TABLE II

| Ex. No. | A | E | G | $R_f$* | m.p. °C. |
|---|---|---|---|---|---|
| VI | —OCH₃ | —CH₂— | phenyl | 0.27³ | |
| VII | —OCH₃ | —CH(CH₃)— | 4-OCH₃-phenyl | 0.16/0.21³ | |
| VIII | H | —CH₂— | phenyl | 0.31⁴ | |
| IX | —OCH₃ | bond | cyclooctyl | 0.63⁴ | |
| X | —OCH₃ | —(CH₂)₃—CH(CH₃)— | —C₆H₅ | | yellowish oil |
| XI | —OCH₃ | —(CH₂)₄— | —C₆H₅ | | colourless oil |

Example XIII

N-(8-Methoxy-chroman-2-yl)methyl-cycloheptane-carboxamide

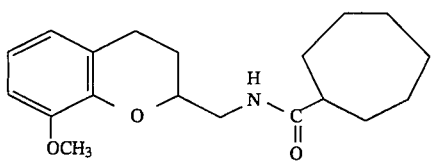

The title compound is prepared analogously to the instructions of Example XII from 2-aminomethyl-8-methoxychroman and cycloheptanecarbonyl chloride, and is further reacted directly.

m.p. ° C.: 135

Example XIV

2-(R)-{N-([1-(R)-1-phenethyl]-N-[4-[4-(4-phenoxybutyloxy)-phenyl]-butyl}]-aminomethyl-8-methoxychroman hydrochloride

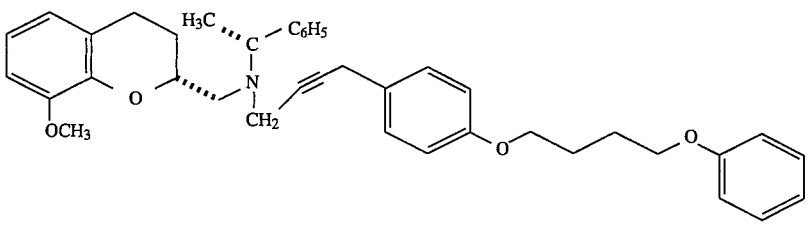

The 2-(R)-2-{N-[1-(R)-phenethyl]}-aminomethyl-8-methoxychroman which is obtainable from (R)-phenylethylamine analogously to EP 352 613/Example 93 is reacted with 3-[4-(4-phenoxybutoxy)phenyl]-propine and paraformaldehyde in the presence of Cu(II) acetate in dioxane at 50° C. After purification by chromatography and precipitation of the hydrochloride, the desired intermediate product is obtained in a yield of 63% as a colourless, amorphous solid.

$R_f$=0.14 (toluene/petroleum ether 1:1)

Example XV

(2S)-2-[N-Cycloheptylmethyl-N-((1R)-1-phenethyl)]-aminomethyl-chroman hydrochloride

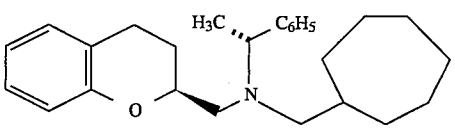

4.3 g of the compound from Example I are taken up in 25 ml of toluene, and 22 g of a 3.4M solution of sodium bis-(2-methoxyethoxy)-dihydroaluminate in toluene are added. After stirring at 50° C. for 1 hour and cooling to room temperature, the mixture is diluted with 50 ml of toluene, and about 5 ml of water are added, until the evolution of gas has ended. The reaction mixture is filtered over silica gel (rinsing with toluene/ethyl acetate 30:1). The free base obtained after concentration of the product-containing fractions is converted into the hydrochloride with ethereal hydrochloric acid.

$R_f$=0.92 (toluene/ethyl acetate 3:1)

The compounds shown in Table III are prepared analogously to the instructions of Example XV:

TABLE III

| Ex. No. | X | Y | —E—G | $R_f$* | m.p. °C. |
|---|---|---|---|---|---|
| XVI | H | H₃C⋯C(C₆H₅)—CH₂—N— | cycloheptyl-CH₂— | | 178/180 (hydrochloride) |
| XVII | —OCH₃ | H₃C⋯C(C₆H₅)—CH₂—N— | cycloheptyl-CH₂— | | |

TABLE III-continued

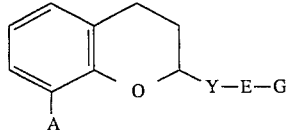

| Ex. No. | X | Y | —E—G | $R_f$* | m.p. °C. |
|---|---|---|---|---|---|
| XVIII | —OCH$_3$ | 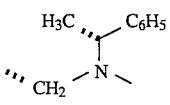 | 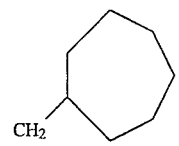 | 0.82³ | |

Example XIX

N-(8-Methoxychroman-2-yl-methyl)-cyclohexane-carboxamide

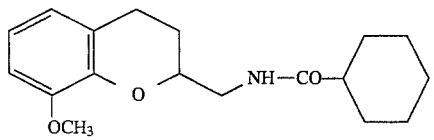

A mixture of 9.5 g (49 mmol) of 2-aminomethyl-8-methoxychroman and 4.9 ml (49 mmol) of triethylamine in 50 ml of anhydrous methylene chloride is added dropwise to a solution of 7.2 g (49 mmol) of cyclohexanecarbonyl chloride in 75 ml of anhydrous methylene chloride, while stirring and cooling with ice. After the mixture has been left to stand overnight, it is poured onto ice. Separation of the phases, extraction of the aqueous phase with methylene chloride, washing with saturated sodium chloride solution and drying of the combined organic phases over anhydrous sodium sulphate gives, after evaporation under a water pump vacuum, 14.5 g of crude amide, which is recrystallised from 160 ml of ethyl acetate. IR (KBr): 3307, 2931, 1642, 1485 and 1256 cm m.p.: 149°–151° C.

The compounds shown in Tables IV, V, VI and VII are prepared analogously to the instructions of Example XIX:

TABLE IV

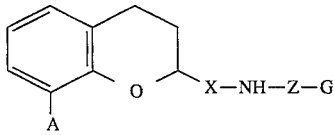

| Ex. No. | A | X | Z | G | m.p. °C./b.p. |
|---|---|---|---|---|---|
| XX | —OCH$_3$ | —CH$_2$— | —CO— |  | colourless oil |
| XXI | —OCH$_3$ | —CH$_2$— | —CO— |  | 146–148 (from ethyl acetate) |
| XXII | —OCH$_3$ | —CH$_2$— | —CO— | 1-adamantyl | waxy oil |
| XXIII | H | —CH$_2$— | —CO— |  | 107.5–109 (from ethyl acetate) |

TABLE IV-continued

| Ex. No. | A | X | Z | G | m.p. °C./b.p. |
|---|---|---|---|---|---|
| XXIV | H | —CH₂— | —CO— |  | 96–103 |
| XXV | H | —CH₂— | —CO— | 1-adamantyl | waxy oil |
| XXVI | H | —CO— | —CH₂— | 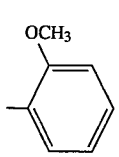 | colourless oil |
| XXVII | H | —CO— | —CH₂— | 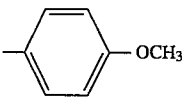 OCH₃ | 170–179 (0.1–0.45 mbar) |
| XXVIII | H | —CO— | —CH₂— | 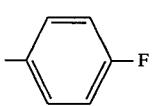 OCH₃ | 175–185 (0.2 mbar) |
| XXIX | H | —CO— | —CH₂— | 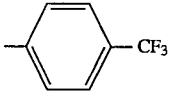 F | colourless oil |
| XXX | H | —CO— | —CH₂— | 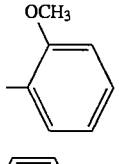 CF₃ | 114 |
| XXXI | —OCH₃ | —CO— | —CH₂— | 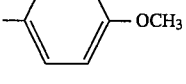 OCH₃ | colourless oil |
| XXXII | —OCH₃ | —CO— | —CH₂— | 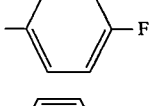 OCH₃ | 128–129 (from methanol) |
| XXXIII | —OCH₃ | —CO— | —CH₂— | 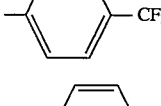 F | colourless oil |
| XXXIV | —OCH₃ | —CO— | —CH₂— | 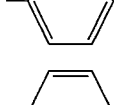 CF₃ | 145–146 (from ethanol) |
| XXXV | H | —CO— | —(CH₂)₃—CH(CH₃) | 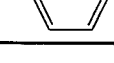 | 160–170 (0.04 mbar) |
| XXXVI | H | —CO— | —(CH₂)₄— | 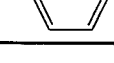 | colourless oil |

TABLE V

Structure: chroman with A substituent on benzene ring, and -CH₂-NH-CO-G at the 2-position.

| Ex. No. | A | G | m.p. °C./b.p. |
|---|---|---|---|
| XXXVII | 8-OCH₃ | —(CH₂)₃—cyclohexyl | 121–123 |
| XXXVIII | 8-OCH3 | —CH₂—cyclohexyl | 143–145 |
| XXXIX | 8-OCH3 | —(CH₂)₂—cyclohexyl | 116–117 |
| XL | 5-OCH₃ | cycloheptyl | 108–110 |

TABLE V-continued

| Ex. No. | A | G | m.p. °C./b.p. |
|---|---|---|---|
| XLI | 8-OCH₃ | cyclooctyl | 112–114 |
| XLII | H | —(CH₂)₂—cyclohexyl | yellow oil |
| XLIII | H | —CH₂—cyclohexyl | 116–120 |
| XLIV | H | —(CH₂)₃—cyclohexyl | yellow oil |

TABLE VI

Structure: chroman with A and B substituents on benzene ring, and -CH₂-NH-CO-G at the 2-position.

| Ex. No. | A | B | G | m.p. °C./b.p. |
|---|---|---|---|---|
| XLV | 7-OCH₃ | H | cycloheptyl | yellow oil |
| XLVI | 7-OCH3 | 8-OCH₃ | —CH₂—cycloheptyl | 95.5–97.5 |
| XLVII | 8-OCH3 | H | —CH₂—cycloheptyl | colourless oil |
| XLVIII | 6-OCH₃ | 7-OCH₃ | cycloheptyl | 140–142 |
| XLIX | 7-OCH₃ | 8-OCH₃ | cycloheptyl | brown oil |

TABLE VI-continued

| Ex. No. | A | B | G | m.p. °C./b.p. |
|---|---|---|---|---|
| L | —OCH(CH$_3$)$_2$ | H | (cycloheptyl) | 139–140 |
| LI | H | H | (methylcyclooctyl) | colourless oil |
| LII | H | H | (1-methylcyclohexyl) H$_3$C | colourless oil |
| LIII | 8-CH$_3$ | H | (cycloheptyl) | 101–103.5 |
| LIV | H | H | —CH$_2$—(cycloheptyl) | 89–91 |
| LV | 6-OCH3 | H | (cycloheptyl) | 108 |

Example LVII 2-(N-Benzylpiperidine-4-carbonyl)-aminomethyl-3,4-di-hydro-2H-1-benzopyran

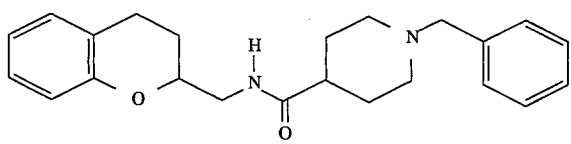

5.0 g (23 mmol) of N-benzylpiperidine-4-carboxylic acid are suspended in 31 ml of dry tetrahydrofuran, and a solution of 4.1 g (25.3 mmol) of 1,1'-carbonyl diimidazole and 62 ml of dry tetrahydrofuran is added dropwise at 20°–25° C. in the course of 30 minutes. When the evolution of carbon dioxide has ended (after about 1 hour), the mixture is further stirred for an additional hour and a solution of 4.5 g (27.5 mmol) of 2-aminomethyl-3,4-dihydro-2H-1-benzopyran and 31 ml of dry tetrahydrofuran is added dropwise in the course of 30 minutes. The mixture is then stirred at room temperature for a further 18 hours. For working up, the mixture is stirred into a mixture of 1.25 l of 5% strength sodium chloride solution, 56 ml of 1 molar hydrochloric acid and 0.6 l of toluene. After the aqueous phase has been extracted once more with 0.3 l of toluene, the combined organic phases are extracted with 300 ml of 0.1 molar hydrochloric acid. After the aqueous phase has been removed, the product starts to crystallise out of the organic phase as the hydrochloride, and can be filtered off with suction and dried.

Yield: 7.4 g (77% of theory) m.p.: 161°–162° C.

The hydrochloride can be converted into the base from an aqueous solution using sodium hydroxide solution. After extraction with toluene and after concentration of the toluene solution to about 70 ml, the base can be crystallized by dropwise addition of 140 ml of petroleum benzine.

Yield: 5.7 g (68% of theory) m.p.: 122°–123° C. Thin layer chromatography: ethyl acetate/ethanol 90:10 R$_f$=0.28

Preparation Examples

EXAMPLE 1

S-(+)-2-(N-Cycloheptylmethyl)aminomethyl-chroman hydrochloride

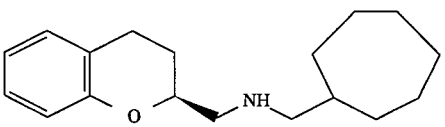

3.2 g (7.7 mmol) of (2S)-2-[N-cycloheptylmethyl-N-((1R)-1-phenethyl)]aminomethyl-chroman hydrochloride are dissolved in 40 ml of methanol and the solution is stirred with 0.5 g of 10% strength Pd on active charcoal. After 15 minutes, the mixture is filtered, the same amount of catalyst and 11 ml of concentrated hydrochloric acid are added and the mixture is diluted with 15 ml of methanol. The mixture is hydrogenated under normal pressure at room temperature for 3 hours. The catalyst is filtered off and the filtrate is concentrated. The base is obtained therefrom by treatment with sodium bicarbonate solution and extraction with ethyl acetate. Chromatography on silica gel (methylene chloride/ethanol/triethylamine 400:10:1) gives 1.5 g of crude free base. The hydrochloride is obtained therefrom by treatment with ethereal hydrochloric acid and is recrystallised from acetonitrile.

Yield: 1.15 g of colourless crystals (48%) m.p.: 177°–178° C. (after recrystallisation from acetonitrile) $R_f$=0.50 (silica gel: methylene chloride/ethanol/ammonia 200:10:1 IR (KBr): 3374, 2920 (b), 1582, 1489, 1456 $\alpha_D$ (c=1, methanol): +94.6°

The compounds shown in Table 1 are prepared analogously to the instructions of Example 1: (the products are always the hydrochlorides.)

32.8 g (95 mmol) of N-(1-naphthylmethyl)-8-methoxychroman-2-carboxamide are added in several portions at 50° C. to 85 g of a 3.4M solution of sodium bis(2-methoxyethoxy)-dihydroaluminate in toluene, diluted with 100 ml of dry toluene. After the mixture has been stirred at this temperature for 2 hours, it is diluted with 150 ml of toluene and hydrolysed dropwise with a mixture of 20 ml of tetrahydrofuran and 8 ml of water. The reaction mixture is filtered over about 50 g of silica gel $K_{60}$. The filtrate is concentrated and the crude product is purified by flash chromatography (silica gel, toluene/ethyl acetate 100:0 to 2:1). This gives 31.8 g (quantitative) of the title compound as the free base. The hydrochloride is obtained from 1.0 g of this base by treatment with ethereal hydrochloric acid and is recrystallised from 2-propanol/diethyl ether.

Yield: 0.84 g of colourless crystals. m.p.: 145°–147° C. (after recrystallisation from 2-propanol/diethyl ether) $R_f$=0.10 (silica gel, toluene/ethyl acetate 1:1)

The compounds shown in Table 2 are prepared analogously to the instructions of Example 5: (the products are always the hydrochlorides.)

TABLE 1

![Structure: chroman with A substituent, Y—NHCH2—G, x HCl]

| Ex. No. | A | Y | G | $R_f$*/optical rotation° m.p. °C. | Starting compound |
|---|---|---|---|---|---|
| 2 | H | ′′′CH₂— | cycloheptyl | 0.50¹ $\alpha_D$–97.9 (c = 1, 1, CH₃OH) 176–177 | XII |
| 3 | —OCH₃ | ◄CH₂— | cycloheptyl | 0.50¹ $\alpha_D$+97.5 (c = 1, CH₃OH) 150 | XVII |
| 4 | —OCH₃ | ′′′CH₂— | cycloheptyl | 0.27² $\alpha_D$–99 (c = 0.9, CH₃OH) 150 | XVIII |

EXAMPLE 5

2-[N-(1-Naphthylmethyl)]aminomethyl-8-methoxy-chroman hydrochloride

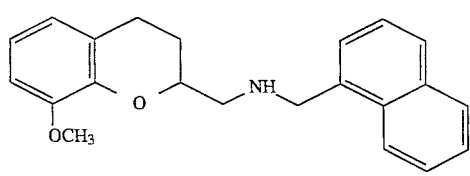

TABLE 2

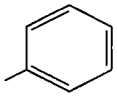

| Ex. No. | A | Y | G | m.p. °C. | Starting compound |
|---|---|---|---|---|---|
| 6 | —OCH₃ | —CH₂— |  | 167 | VI |
| 7 | —OCH₃ | —CH(CH₃)— | 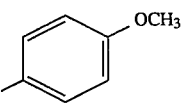 (OCH₃) | 228 | VII |
| 8 | H | —CH₂— | 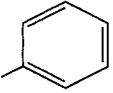 | 201–203 | VIII |
| 9 | —OCH₃ | bond | 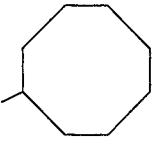 | 167 | IX |

EXAMPLE 10

2-(N-Cycloheptylmethyl)aminomethyl-chroman hydrochloride

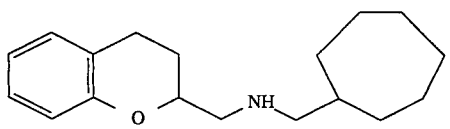

25 mmol of the compound from Example XII are added in portions to a mixture of 20 g (73 mmol) of a 70% strength solution of sodium bis-(2-methoxyethoxy)-di-hydroaluminate in toluene and 30 ml of toluene under argon. After 1 hour at 50° C. the mixture is cooled in an ice-bath and diluted with 30 ml of toluene. Ice is added in small portions until the evolution of gas has ended, and this is followed by addition of about 5 ml of 45% strength sodium hydroxide solution. Flash chromatography (silica gel, ethyl acetate) of the reaction mixture gives the free base as a syrup. 5.2 g (67%, based on the 2-aminomethylchroman employed) of the hydrochloride are obtained therefrom by treatment with ethereal hydrochloric acid.

m.p.: 194°–195° C. (after recrystallisation from acetonitrile) IR (KBr): 2929, 2854, 2743(b), 1594

The compound shown in Table 3 is prepared analogously to the instructions of Example 10: (the compound is in the form of the hydrochloride.)

TABLE 3

| Ex. No. | A | E | G | m.p. °C. | Starting compound |
|---|---|---|---|---|---|
| 11 | —OCH₃ | —CH₂— | (cycloheptyl) | 166–168 | XIII |

EXAMPLE 12

2-(R)-2(N-Cycloheptylmethyl)aminomethyl-8-hydroxychroman hydrochloride

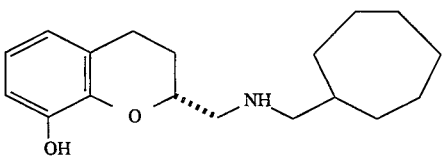

1.7 g (5.0 mmol) of 2-(R)-2-(N-cycloheptylmethyl)aminomethyl-8-methoxy-chroman hydrochloride are heated under reflux with 50 ml of 48% strength hydrobromic acid for 4.5 hours. The product which precipitates after the mixture has cooled to room temperature is filtered off with suction and washed with water. The base is liberated by treatment with sodium bicarbonate solution/ethyl acetate. The organic phase is dried (magnesium sulphate) and concentrated. The hydrochloride is obtained from this residue by reaction with ethereal hydrochloric acid. Recrystallisation from 2-propanol gives 0.58 g (36%) of colourless crystals.

m.p.: 250°–251° C. (after recrystallisation from 2-propanol) $R_f$=0.30 (silica gel; methylene chloride/ethanol/ammonia 200:10:1) IR (KBr): 3252(b), 2924, 2855, 1595, 1484 $\alpha_D$ (c=1, methanol): –109.7° C.

EXAMPLE 13

2-(R)-2-(N-Cycloheptylmethyl-N-methyl)aminomethyl-8-methoxy-chroman hydrochloride

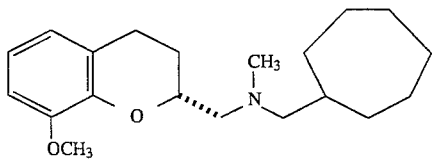

The base is liberated from 1.7 g (5 mmol) of 2-(R)-2-(N-cycloheptylmethyl)aminomethyl-8-methoxy-chroman hydrochloride and is dissolved in 25 ml of dioxane. 25 ml of an aqueous 1M solution of NaH$_2$PO$_3$ and 2.5 ml of a 35% strength aqueous formaldehyde solution are added. After 15 minutes at 60° C., the mixture is cooled and poured onto a mixture of in each case 100 ml of saturated sodium bicarbonate solution and ethyl acetate. The aqueous phase is extracted with ethyl acetate. The combined organic extracts are dried (magnesium sulphate) and concentrated. Chromatography (silica gel, methylene chloride/ethanol/triethylamine 400:10:1) gives the free base, which is converted into the hydrochloride by treatment with ethereal hydrochloric acid. Recrystallisation from acetonitrile gives 0.45 g (28%) of colourless crystals. m.p.: 203°–204° C. (after recrystallisation from acetonitrile) $R_f$=0.24 (silica gel, methylene chloride/ethanol/ammonia 400:10:1) IR (KBr): 3422(b), 2924, 2853, 2560(b), 1587, 1486, 1467 $\alpha_D$ (c=0.9, methanol): –92.2°

EXAMPLE 14

2-(R)-{4-[4-(4-Phenoxybutoxy)phenyl]butyl}-aminomethyl- 8-methoxy-chroman hydrochloride

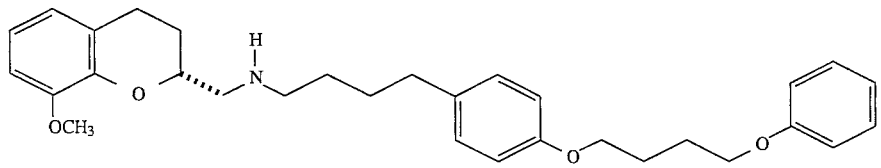

3.95 g (6.7 mmol) of 2-(R)-(2-{N-[1-(R)-1-phenethyl-N-{4-[4-(4-Phenoxybutoxy)phenyl]butyl}}aminomethyl-8-methoxy-chroman chroman hydrochloride in 40 ml of methanol are stirred with 1 g of 5% strength Pd/C. After filtration, 13.4 ml of concentrated hydrochloric acid and 1.0 g of 5% strength Pd on active charcoal (suspended in 10 ml of methanol) are added to the filtrate. Hydrogenation is carried out under normal pressure for 4 hours. The reaction mixture is diluted with 40 ml of tetrahydrofuran and 100 ml of methylene chloride and filtered over kieselguhr. Concentration until crystallisation starts gives, after the mixture has been left to stand overnight, 1.6 g of crude product, which is recrystallised first from methanol and then from 2-propanol. Yield: 0.80 g (23%) of colourless crystals m.p.: 125° C. $R_f$=0.44 (silica gel, methylene chloride/methanol 10:1)

EXAMPLE 15

2-N-(1,4-Dioxaspiro[4,5]decan-8-yl)aminomethyl-8-methoxychroman hydrochloride

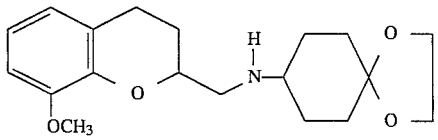

The base is liberated from 2.3 g (10 mmol) of 2 -aminomethyl-8-methoxychroman hydrochloride with sodium bicarbonate. This base is dissolved in 30 ml of methanol, and 1.2 g (20 mmol) of acetic acid and 3.2 g (20 mmol) of 1,4-dioxaspiro[4,5 ]-decan-8-one are added. After addition of 10 g of molecular sieve (4 Å), the mixture is stirred at room temperature for 30 minutes and then at 50° C. for 30 minutes. After cooling to 0° C., 1.3 g of sodium cyanoborohydride are added. The reaction mixture is heated at 50° C. for 2 hours. After cooling to room temperature, it is filtered and the filtrate is concentrated. The residue is partitioned between 1N sodium hydroxide solution and methylene chloride. Drying of the organic phase and concentration gives a crude product, which is purified by flash chromatography (silica gel, toluene/ethyl acetate gradient 100: 0 to 0: 100, then ethyl acetate/2-propanol/triethylamine 75:25:1). The free base of the title compound is obtained as an oil, which is converted into the hydrochloride by treatment with ethereal hydrochloric acid.

Yield: 2.4 g (66%) of colourless crystals m.p.: 236°–237° C. (after recrystallisation from acetonitrile) IR (KBr): 3;510, 2951(b), 2752(b), 1587, 1486

EXAMPLE 16

N-Cyclopentylmethyl-2-aminomethylchroman

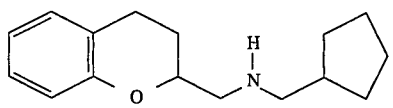

16.0 g (0.06 mol) of N-cyclopentylmethyl-chroman-2-carboxamide in 200 ml of anhydrous tetrahydrofuran are added dropwise to 300 ml of a 1M borane/tetrahydrofuran solution (0.3 mol) at 0° to −10° C. in the course of 30 minutes, while stirring and under argon. The mixture is stirred at 20° C. for 2 hours and then at 60° C. for 6 hours. After being left to stand overnight, 80 ml of 10% strength hydrochloric acid are added dropwise. After the mixture has been subsequently stirred at 20° C. for 3 hours, it is evaporated to dryness under a water pump vacuum. The residue is rendered alkaline with 10% strength sodium hydroxide solution. Extraction with methylene chloride, washing of the combined methylene chloride extracts with saturated sodium chloride solution and evaporation of the extract which has been dried over anhydrous sodium sulphate gives 16.0 g of crude amine. Distillation gives 11.5 g of the title compound of boiling point 120°–126° C./0.2–0.25 mmHg.

EXAMPLE 17

N-Cyclohexylmethyl-2-aminomethyl-8-methoxy-chroman hydrochloride

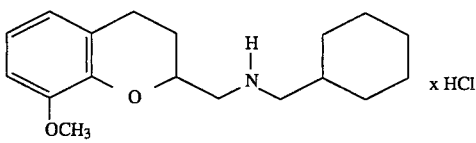

9.3 ml of a 2.7M hydrogen chloride solution in diethyl ether are added to 7.2 g (15 mmol) of N-cyclohexylmethyl-2-aminomethyl-8-methoxychroman in 200 ml of diethyl ether at 0° to −10° C., while stirring. After 2 hours, the precipitate is filtered off, washed thoroughly with diethyl ether and dried at 60° C./0.01 mbar.

Yield: 6.6 g (81%) m.p.: 188°–191° C.

The compounds shown in Tables 4, 5, 6, 7, 8, 9 and 10 are prepared analogously to the instructions given above:

TABLE 4

| Ex. No. | A | $R^1$ | −E−G | m.p. °C. | Preparation analogous to Example (No.) |
|---|---|---|---|---|---|
| 18 | H | H | −(CH$_2$)$_3$−CHC$_6$H$_5$ \| CH$_3$ | 188.5–191 | 17 |
| 19 | H | H | −CH$_2$−O−H$_3$CO−C$_6$H$_4$ | 161.5–164.5 | 17 |
| 20 | H | H | −CH$_2$−P−H$_3$CO−C$_6$H$_4$ | 194–196 | 17 |
| 21 | H | H | −CH$_2$−P−F−C$_6$H$_4$ | 215–217 | 17 |
| 22 | −OCH$_3$ | H | −CH$_2$−P−F$_3$C−C$_6$H$_4$ | 193–195 | 17 |
| 23 | −OCH$_3$ | H | −CH$_2$−P−H$_3$CO−C$_6$H$_4$ | 153.5–155.5 | 17 |
| 24 | −OCH$_3$ | H | −CH$_2$−O−H$_3$CO−C$_6$H$_4$ | 145–149 | 17 |
| 25 | −OCH$_3$ | H | −CH$_2$−P−F−C$_6$H$_4$ | 163–166 | 17 |
| 26 | H | H | −CH$_2$−P−F$_3$C−C$_5$H$_4$ | 223–228 | 17 |
| 27 | −OCH$_3$ | H | −CH$_2$−cyclopropyl | 180–182.5 | 17 |
| 28 | H | H | −CH$_2$−cyclopropyl | 190–206 | 17 |
| 29 | H | H | −CH$_2$−C$_6$H$_{11}$ | 184–186 | 17 |
| 30 | H | H | −(CH$_2$)$_4$−C$_6$H$_5$ | 202–203 | 17 |
| 31 | H | H | −CH$_2$-adamant-1-yl | 194–198 | 17 |
| 32 | H | H | −CH$_2$−cyclopentyl | 198.5–201.5 | 17 |
| 33 | −OCH$_3$ | H | −CH$_2$-adamant-1-yl | 250–252 | 17 |
| 34 | −OCH$_3$ | H | −CH$_2$−cyclobutyl | 199–202 | 17 |

TABLE 4-continued

[Structure: chroman with A substituent, CH2-N(R1)-E-G side chain] × HCl

| Ex. No. | A | R¹ | —E—G | m.p. °C. | Preparation analogous to Example (No.) |
|---|---|---|---|---|---|
| 35 | H | —CH₃ | —CH₂-(4-piperidyl)-N-benzyl | 263–264 (dihydrochloride) | 17 |
| 36 | H | H | —CH₂-(4-piperidyl)-N-benzyl | 265–266 (dihydrochloride) | 17 |
| 37 | —OCH₃ | H | —(CH₂)₃—CH(CH₃)—C₆H₅ | 91–94 | 17 |
| 38 | —OCH₃ | H | —(CH₂)₄—C₆H₅ | 128–132 | 17 |

TABLE 5

[Structure: chroman with A substituent, CH2—NH—E—G side chain]

| Ex. No. | A | —E—G | m.p. °C./b.p. °C. | Preparation analogous to Example |
|---|---|---|---|---|
| 39 | H | —CH₂-cyclopropyl | colourless oil | 16 |
| 40 | H | —CH₂-cyclohexyl | 199 (methylene chloride/petroleum ether) | 16 |
| 41 | H | —CH₂-adamant-1-yl | waxy oil | 16 |
| 42 | —OCH₃ | —CH₂-cyclopropyl | pale yellow oil | 16 |
| 43 | —OCH₃ | —CH₂-cyclopentyl | colourless oil | 16 |
| 44 | —OCH₃ | —CH₂-cyclohexyl | colourless oil | 16 |
| 45 | —OCH₃ | —CH₂-adamant-1-yl | waxy oil | 16 |
| 46 | H | —CH₂-(2-methoxyphenyl) | 122–125 0.07 mbar | 16 |

TABLE 5-continued

Structure: chroman with substituent A at 8-position, and -CH₂-NH-E-G at 2-position

| Ex. No. | A | —E—G | m.p. °C./b.p. °C. | Preparation analogous to Example |
|---------|------|------|-------------------|----------------------------------|
| 47 | H | —CH₂—(C₆H₄)—OCH₃ (para) | 145–150 0.04 mbar | 16 |
| 48 | H | —CH₂—(C₆H₄)—F (para) | 115–124 0.06–0.04 mbar | 16 |
| 49 | H | —CH₂—(C₆H₄)—CF₃ (para) | colourless oil | 16 |
| 50 | —OCH₃ | —CH₂—(C₆H₄)—OCH₃ (ortho, H₃CO) | pale yellow oil (decomp.) | 16 |
| 51 | —OCH₃ | —CH₂—(C₆H₄)—OCH₃ (para) | 133–144 0.05–0.03 mbar | 16 |
| 52 | —OCH₃ | —CH₂—(C₆H₄)—F (para) | colourless oil | 16 |
| 53 | —OCH₃ | —CH₂—(C₆H₄)—CF₃ (para) | 156–164 0.1 mbar | 16 |

TABLE 6

Structure: chroman with substituent A at 8-position, and -CH₂-N(R₁)-E-G at 2-position, × HCl

| Ex. No. | A | $R^1$ | —E—G | b.p. °C. | Preparation analogous to Example (No.) |
|---------|---|-------|------|----------|----------------------------------------|
| 54 | H | —CH₃ | —H₂C—(4-piperidinyl)-N-CH₂-C₆H₅ | 210–215 (0.05 mbar) | 13 (use of NaBH₃CN instead of NaH₂PO₃) |
| 55 | H | H | —H₂C—(4-piperidinyl)-N-CH₂-C₆H₅ | 210 (0.05 mbar) | 16 |

TABLE 7

| Ex. No. | A | B | —E—G | m.p. °C. | Preparation analogous to Example (No.) |
|---|---|---|---|---|---|

Structure: chroman with A and B substituents, CH₂—NH—E—G side chain, × HCl

| Ex. No. | A | B | —E—G | m.p. °C. | Preparation analogous to Example (No.) |
|---|---|---|---|---|---|
| 56 | 8-OCH₃ | H | —(CH₂)₄—cyclohexyl | 146–147 | 17 |
| 57 | 8-OCH₃ | H | —(CH₂)₂—cyclohexyl | 158–160 | 17 |
| 58 | 8-OCH₃ | H | —(CH₂)₃—cyclohexyl | 146–147 | 17 |
| 59 | 5-OCH₃ | H | —CH₂—cycloheptyl | 216–220 | 17 |
| 60 | 8-OCH₃ | H | —CH₂—cyclooctyl | 134–136 | 17 |
| 61 | H | H | —(CH₂)₃—cyclohexyl | 182–190 | 17 |
| 62 | H | H | —(CH₂)₂—cyclohexyl | about 210 (decomp.) | 17 |
| 63 | H | H | —(CH₂)₄—cyclohexyl | 214–216 | 17 |
| 64 | 7-OCH₃ | H | —CH₂—cycloheptyl | 161–165 | 17 |
| 65 | 7-OCH₃ | 8-OCH₃ | —CH₂—cycloheptyl | 160–162.5 | 17 |
| 66 | 8-OCH₃ | H | —CH₂—cycloheptyl | 130–132 | 17 |
| 67 | 6-OCH₃ | 7-OCH₃ | —CH₂—cycloheptyl | 157–160 | 17 |

TABLE 7-continued
| Ex. No. | A | B | —E—G | m.p. °C. | Preparation analogous to Example (No.) |
|---|---|---|---|---|---|
| 68 | 7-OCH$_3$ | 8-OCH$_3$ | —CH$_2$—(cycloheptyl) | 134–136.5 | 17 |
| 69 | 8-O—CH(CH$_3$)$_2$ | H | —CH$_2$—(cycloheptyl) | 131 | 17 |
| 70 | H | H | —CH$_2$—(cyclooctyl) | 260–262 | 17 |
| 71 | H | H | —CH$_2$—(1-methylcyclohexyl) | 105–108 | 17 |
TABLE 8
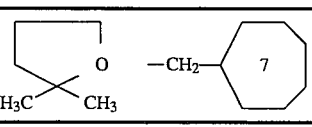
× HCl
| Ex. No. | B | D | -E-G | m.p. °C. | Preparation analogous to Example (No.) |
|---|---|---|---|---|---|
| 72 | 8-CH$_3$ | H | —CH$_2$—(cycloheptyl) | 128–131 | 17 |
| 73 | H | H | —(CH$_2$)$_2$—(cycloheptyl) | 206–209 | 17 |
| 74 | 6-OCH$_3$ | H | —CH$_2$—(cycloheptyl) | 181.5–186 | 17 |
| 75 | (B-D = —C(CH$_3$)$_2$—O— fused ring) | | —CH$_2$—(cycloheptyl) | 183–186 | 17 |

TABLE 9

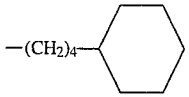

| Ex. No. | A | B | -E-G | m.p. °C. | Preparation analogous to Example (No.) |
|---|---|---|---|---|---|
| 76 | 8-OCH$_3$ | H | —(CH$_2$)$_4$—cyclohexyl | colourless oil | 16 |
| 77 | 8-OCH$_3$ | H | —(CH$_2$)$_2$—cyclohexyl | waxy oil | 16 |
| 78 | 8-OCH$_3$ | H | —(CH$_2$)$_3$—cyclohexyl | colourless oil | 16 |
| 79 | 5-OCH$_3$ | H | —CH$_2$—cycloheptyl | colourless oil | 16 |
| 80 | 8-OCH$_3$ | H | —CH$_2$—cyclooctyl | oil | 16 |
| 81 | H | H | —(CH$_2$)$_3$—cyclohexyl | brown oil | 16 |
| 82 | H | H | —(CH$_2$)$_2$—cyclohexyl | colourless oil | 16 |
| 83 | H | H | —(CH$_2$)$_4$—cyclohexyl | colourless oil | 16 |
| 84 | 7-OCH$_3$ | H | —CH$_2$—cycloheptyl | pale yellow oil | 16 |
| 85 | 7-OCH$_3$ | 8-OCH$_3$ | —(CH$_2$)$_2$—cycloheptyl | brown oil | 16 |
| 86 | 8-OCH$_3$ | H | —CH$_2$—cycloheptyl | oil | 16 |
| 87 | 6-OCH$_3$ | 7-OCH$_3$ | —CH$_2$—cycloheptyl | pale yellow oil | 16 |
| 88 | 7-OCH$_3$ | 8-OCH$_3$ | —CH$_2$—cycloheptyl | colourless oil | 16 |

TABLE 9-continued

| Ex. No. | A | B | -E-G | m.p. °C. | Preparation analogous to Example (No.) |
|---|---|---|---|---|---|
| 89 | 8-O—CH(CH$_3$)$_2$ | H | —CH$_2$—(cycloheptyl) | yellow oil | 16 |
| 90 | H | H | —CH$_2$—(cyclooctyl) | colourless oil | 16 |
| 91 | H | H | —CH$_2$—(cyclohexyl with H$_3$C) | yellow oil | 16 |
| 92 | 8-CH$_3$ | H | —CH$_2$—(cycloheptyl) | colourless oil | 16 |
| 93 | H | H | —(CH$_2$)$_2$—(cycloheptyl) | colourless oil | 16 |
| 94 | 6-OCH$_3$ | H | —CH$_2$—(cycloheptyl) | colourless oil | 16 |

TABLE 10

| Ex. No. | B | D | -E-G | m.p. °C. | Preparation analogous to Example (No.) |
|---|---|---|---|---|---|
| 95 | —CH$_2$C(CH$_3$)$_2$—O— (fused ring with D) | | —CH$_2$—(cycloheptyl) | pale yellow oil | 16 |

We claim:

1. Aminomethyl-chromans of the formula

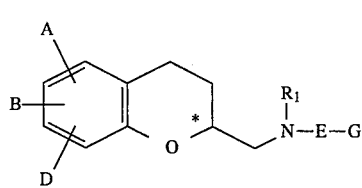

(I)

in which

A, B and D are identical or different and represent hydrogen, fluorine, chlorine, bromine, cyano, trifluoromethyl, trifluoromethoxy or hydroxyl, or represent straight-chain or branched alkyl or alkenyl having in each case up to 4 carbon atoms, or represent a group of the formula —NR$^2$R$^3$ or —OR$^6$, wherein R$^2$ and R$^3$ are identical or different and denote hydrogen or straight-chain or branched alkyl having up to 4 carbon atoms and $R^6$ denotes straight-chain or branched alkyl or alkenyl having up to 4 carbon atoms, which are optionally substituted by cyclopropyl or phenyl, or A has one of the abovementioned meanings and B and D together form a radical of the formula

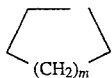

wherein m denotes the number 1 or 2;

E represents a direct bond, or represents straight-chain or branched alkylene or alkenylene having in each case up to 7 carbon atoms, which are optionally substituted by phenyl, G represents phenyl or naphthyl which are optionally substituted by fluorine, chlorine, bromine, hydroxyl, difluoromethyl, trifluoromethyl, difluoromethoxy or trifluoromethoxy or by straight-chain or branched alkyl or alkoxy having in each case up to 4 carbon atoms, the latter optionally being substituted by phenyl or phenoxy, and $R_1$ represents hydrogen or represents straight-chain or branched alkyl having up to 4 carbon atoms, or represents the radical of the formula —E'—G' wherein E' and G' have the meaning given above for E and G and are identical or different from these radicals, or an isomer or salt thereof.

2. A composition for the treatment of diseases which are characterized by disturbances in the serotoninergic system comprising an amount effective therefor of a compound or a salt thereof according to claim 1 and a pharmacologically acceptable diluent.

3. A composition for the treatment of psychoses comprising an amount effective therefor of a compound or salt thereof according to claim 1 and a pharmacologically acceptable diluent.

* * * * *